United States Patent [19]

Ham

[11] 4,276,778

[45] Jul. 7, 1981

[54] ANAEROBIC SAMPLING METHOD

[75] Inventor: Robert K. Ham, Madison, Wis.

[73] Assignee: Getty Synthetic Fuels, Inc., Signal Hill, Calif.

[21] Appl. No.: 123,439

[22] Filed: Feb. 21, 1980

[51] Int. Cl.³ .............................................. G01N 1/04
[52] U.S. Cl. ........................... 73/864.43; 23/230 EP; 73/19; 73/863; 166/250
[58] Field of Search ............. 73/421.5 R, 425, 432 R, 73/424; 166/246, 250; 23/230 EP

[56] References Cited

U.S. PATENT DOCUMENTS

| 3,862,576 | 1/1975 | Pogorski | 73/421.5 R |
| 4,026,355 | 5/1977 | Johnson et al. | 166/246 |
| 4,065,972 | 1/1978 | Holub et al. | 73/421.5 R |
| 4,159,893 | 7/1979 | Ham | 23/230 EP |

Primary Examiner—Donald O. Woodiel
Attorney, Agent, or Firm—Gordon L. Peterson

[57] ABSTRACT

A method of obtaining a substantially anaerobic sample from a landfill comprising providing a bore hole which opens at the surface of the landfill, substantially sealing off atmospheric air from a zone which includes at least a region of the bore hole to define an essentially anaerobic zone. Refuse from the anaerobic zone within the bore hole is loaded into a sample container in the anaerobic zone. The sample container is sealed within the anaerobic zone and then removed from the anaerobic zone. The sample can be used for various tests, including a determination of the rate of landfill gas generation by the sample.

21 Claims, 4 Drawing Figures

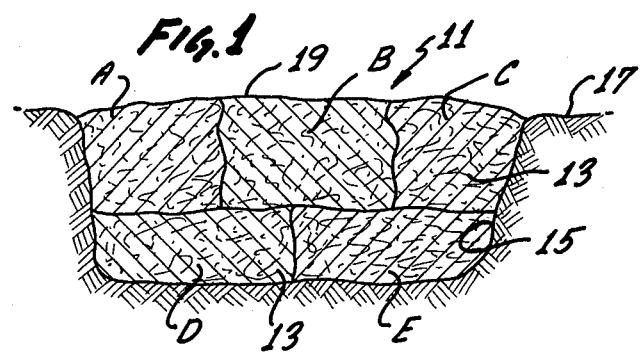
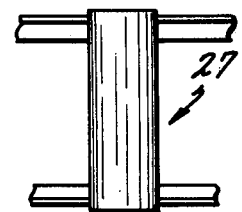
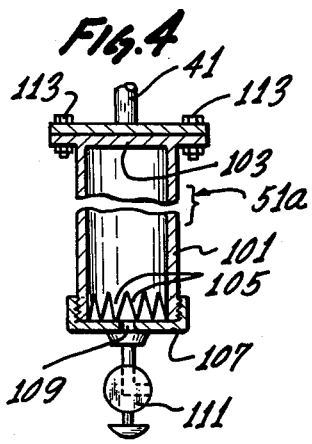
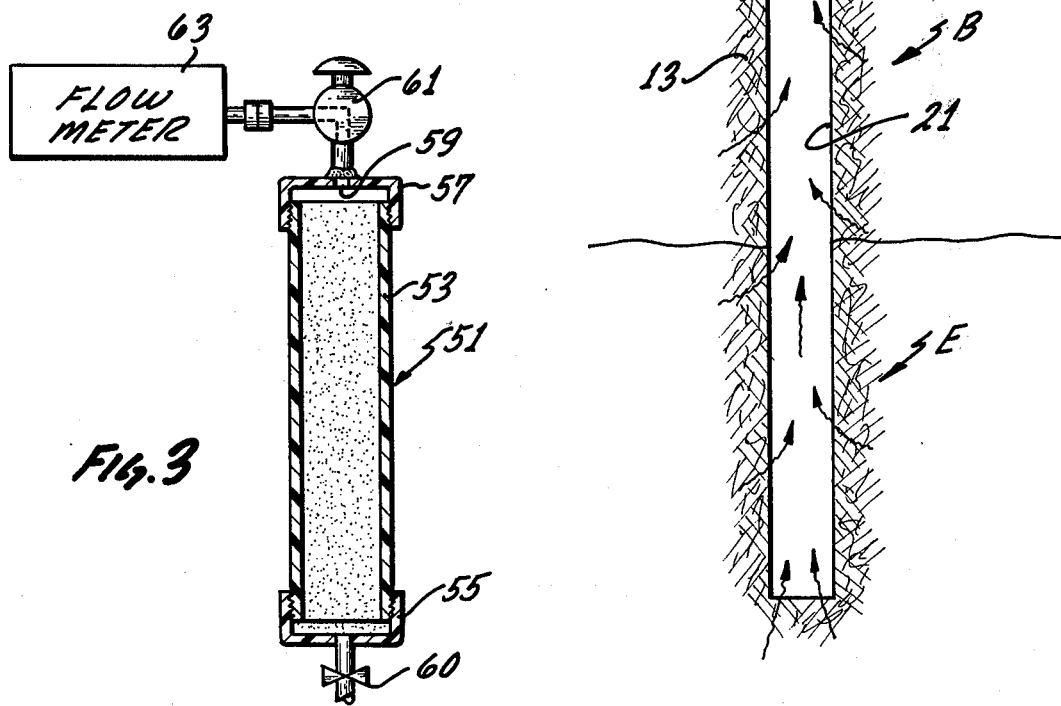

ANAEROBIC SAMPLING METHOD

BACKGROUND OF THE INVENTION

Decomposition of refuse within a landfill produces landfill gas which contains methane. In some instances, the methane concentration is sufficient to warrant recovery of the landfill gas so that the methane can be used as a fuel. To increase the concentration of the methane, a methane purification plant can be installed at the landfill.

The recovery of landfill gas and its purification requires a very substantial investment for the construction of the necessary recovery and purification plant. Before making an investment of this magnitude, it is imperative to make numerous determinations regarding properties of the landfill gas, including, among other things, the composition of the landfill gas, the total volume of the landfill gas which the landfill can produce and whether or not the rate of landfill gas generation by the landfill is sufficient to warrant the installation of the recovery and purification plant. The landfill gas generation rate is the rate at which the landfill or a quantity of refuse produces landfill gas, and it may be measured, for example, in cubic feet per minute per given volume or weight of refuse.

Also, the rate of landfill gas generation must be known so that the allowable withdrawal rate of the landfill gas from the landfill can be ascertained. If the withdrawal rate of the landfill gas in the landfill exceeds the landfill gas generation rate, air will be drawn into the landfill through the surface of the landfill. An entry into the landfill is totally intolerable because the oxygen poisons the micro-organisms which are essential to the production of methane by the landfill. Accordingly, air entry into the landfill as a result of overestimating the rate of gas generation must be completely avoided.

Landfills may extend over many acres and contain huge volumes of refuse. For this reason, it is impossible to directly measure the rate of landfill gas generation of the entire landfill.

One prior art attempt at determining the instantaneous rate of gas generation from refuse is to place new refuse in a lysimeter, drip water through the lysimeter and measure the gas generated. Although experiments of this type are of interest in a laboratory, they have been found to be essentially useless for determining the rate of landfill gas generation by a landfill.

Another prior art method is disclosed in Johnson et al U.S. Pat. No. 4,026,355. Although this method has been used satisfactorily, it requires the installation of a multiplicity of wells and probes in the landfill.

Another disadvantage of these prior art methods is that they do not provide any way to determine the effect of certain variables on properties of the landfill gas. For example, it is sometimes necessary or desirable to determine whether the addition of a different kind of refuse not previously deposited in the landfill will adversely affect the landfill gas generation rate. Conversely, it may be desirable to determine whether a particular material may act as a stimulant to increase the gas generation rate. It is, of course, not feasible to expose the entire landfill to the new ingredient because, if it adversely affects the rate of gas generation or gas composition, a substantial fuel loss from the landfill will occur. Other variables which must also be considered include temperature and moisture flow within the landfill.

SUMMARY OF THE INVENTION

This invention solves the problems discussed above. This invention provides a method of obtaining a substantially anaerobic sample of refuse from a landfill. The sample is then used to simulate in the laboratory the degradation processes which occur in the landfill. The landfill gas from the sample can be used in the laboratory, for example, to determine the rate of landfill gas generation, the total amount of landfill gas which can be generated and landfill gas composition. In addition, the effect of certain variables on the landfill gas can be determined.

The taking of a sample of refuse of the landfill without introducing oxygen from the atmosphere into the sample is difficult. As indicated above, if oxygen is introduced into the sample, the micro-organisms are poisoned by it, and consequently, the sample no longer reflects the true gas generation rate which would exist under anaerobic conditions.

According to this invention, a bore hole is drilled in the landfill with the bore hole opening at the surface of the landfill. Atmospheric air is then substantially excluded from an anaerobic zone which includes at least a region of the bore hole. Refuse from the anaerobic zone within the bore hole is loaded into a sample container. The sample container is sealed within the anaerobic zone and then removed from the anaerobic zone.

The landfill gas produced by the refuse flows into the bore hole and is at a pressure which is above atmospheric pressure. This invention uses this characteristic of the landfill to advantage.

For example, to provide the anaerobic zone, a flexible sheet can be placed over the opening of the bore hole. Because the anaerobic zone is under a positive pressure and any leakage will be outwardly, the sheet may have opening means in that it may be gas pervious, have one or more openings therein, and/or not be sealed to the surface of the landfill around the opening of the bore hole. In addition, the positive pressure in the bore hole is used to elevate the sheet, to effectively inflate the anaerobic zone.

In addition, this positive pressure within the anaerobic zone can be used to purge any air which may be within the anaerobic zone at the instant that the flexible sheet is placed over the opening of the bore hole. The landfill gas carries the air outwardly through the opening in the sheet. If it is believed that any significant amount of air exists in the anaerobic zone at the moment of placement of the sheet over the opening of the bore hole, the refuse sample should not be taken for a short time, such as a few minutes, until an oxygen meter indicates that the oxygen level is below the acceptable maximum level within the anaerobic zone.

The refuse can be loaded into the sample container in different ways. For example, an open-ended sample container may be forced into the refuse within the anaerobic zone to provide a sample within the sample container. Alternatively, the refuse from within the anaerobic zone may be manually loaded into the sample container.

In order to manually load the refuse into the sample container, it is necessary to loosen refuse from the anaerobic zone. This is preferably carried out with an appropriate tool, such as an auger. For example, the refuse may be loosened by rotating an auger against some of the refuse at a first location in the bore hole. The auger then elevates at least some of the loosened refuse to a second location adjacent a workman so that the manual loading function can be carried out at that location. This enables a workman within the anaerobic zone adjacent the surface of the landfill to obtain and manually load a sample of refuse taken from a much lower elevation in the bore hole.

Manual loading of the refuse into the sample container assures that the container will be completely filled with refuse and that it will not inadvertently fall out of the container. In addition, this enables the sample container to be manually sealed within the anaerobic zone to positively exclude contamination of the sample by oxygen. Because the sample has been previously loosened and is manually loaded, the likelihood of obtaining nominally identical samples is increased.

Once the sample is securely sealed within the sample container, the sample container is removed from the anaerobic zone. Thereafter, the sample may be subjected to various testing with substantial certainty that the sample has not been poisoned by oxygen contact.

One of the most useful tests performed on the anaerobic landfill sample is measuring the rate of generation of landfill gas by the sample. This can be accomplished, for example, by coupling a flow meter to the sample container and allowing the landfill gas produced by the sample to escape from the sample container through the flow meter.

In addition, the sample may be subjected to variables, such as temperature changes, moisture flow or a known material in order to determine what effect, if any, the variable will have on the gas generation rate or gas composition of the sample. For example, the known material may be water, a waste which it is desired to deposit in the landfill or a material which is expected to stimulate gas generation by the refuse. In either event, if it is determined that the known material reduces the gas generation rate or adversely affects landfill gas composition, only the small sample is lost and there has been no risk to the fuel-generating capability of the entire landfill as a result of the test.

Unfortunately, landfills are not homogeneous in that the refuse within a landfill varies widely and may include, for example, paper, wood, metal, plastics, etc. Accordingly, to determine the rate of landfill gas generation, the landfill is divided into sections with each significant portion of the landfill which acts substantially uniformly with respect to the rate of landfill gas generation forming one section. Only portions of the landfill which are significant in terms of methane production are dealt with because it would be totally impractical to consider all quantities of the landfill.

Any characteristic which indicates that a different landfill gas generation rate is likely can be used to identify a section. For example, time of placement of the refuse in the landfill and water content can be used. Also, the upper layer of the landfill may be considered as a separate section if it is believed that the upper layer may respond differently to weather variations or if it is believed that air may have infiltrated into the upper layer. The different sections may be selected substantially in accordance with the parameters set forth in Ham U.S. Pat. No. 4,159,893.

After locating the relevant sections, at least one sample of the material of the landfill is taken from each of the sections substantially without introducing oxygen from the atmosphere into the sample. Although various different sampling techniques may be utilized, it is preferred to utilize the anaerobic sampling method described hereinabove.

The rate of landfill gas generation from each of the samples is then measured without introducing oxygen from the atmosphere into the samples. The measured rates are then used to project the rate of landfill gas generation by the landfill. This can be accomplished, for example, by multiplying the gas generation rate per pound of refuse as obtained from the samples by the number of pounds in the associated section and then summing these products for all of the sections. Of course, various known statistical techniques may be used to assure that the measured landfill gas generation rate obtained from the samples is representative of the refuse in that associated section. For example, a number of samples can be obtained from each section at different locations within the section, and certain of the samples discarded and/or the results from the individual samples averaged or otherwise statistically processed to assure a more accurate result.

The invention, together with further features and advantages thereof, may best be understood by reference to the following description taken in connection with the accompanying illustrative drawing.

BRIEF DESCRIPTION OF THE DRAWING

FIG. 1 is a sectional view of a landfill on which the process of this invention can be carried out.

FIG. 2 is a sectional view through a portion of the landfill illustrating the anaerobic sampling technique of this invention.

FIG. 3 is a sectional view through a typical sample container with the sample container coupled to a flow meter to provide a measurement of the rate of landfill gas generation.

FIG. 4 is a fragmentary sectional view illustrating another form of sample container.

DESCRIPTION OF THE PREFERRED EMBODIMENT

FIG. 1 shows a sanitary landfill 11 of the type on which the process of this invention is adapted to be carried out. The landfill 11 is of the type in which anaerobic decomposition produces a landfill gas which includes methane. Although the landfill 11 can be formed in different ways, in the form shown in FIG. 1, it is formed by depositing refuse 13 in a cavity or excavation 15 in the earth 17. Descriptions of the various types of landfill designs are well covered in the solid waste disposal literature. The landfill 11 has an upper surface 19 which is exposed at the top of the landfill. Although the landfill 11 is of the type in which the refuse 13 is deposited in an excavation, the process of this invention is equally applicable to other kinds of landfills, such as landfills described in the literature referred to above.

If it is desired to determine the landfill gas generation rate of the entire landfill 11, sections, such as sections A, B, C, D and E of the landfill, are identified and located. Each significant portion of the landfill 11 which acts substantially uniformly with respect to the rate of landfill gas generation is identified as one of the sections A-E. The number of sections selected and identified for a given landfill will vary in accordance with the characteristics of the landfill. In addition, more accurate results should be obtainable with the process as the number of sections selected for a given landfill increases. On the other hand, the time and expense in carrying out the process of this invention will also increase as the number of sections selected increases.

Each of the sections A–E is distinguishable from the other sections by at least one characteristic. Although different characteristics, such as moisture, type of waste and local growth conditions may be utilized, in the landfill 11, the characteristic which distinguishes each of the sections A–E is time of placement in the landfill. The sections A–E were placed in the landfill in order of section E to section A, with the section E being placed first.

Although the selection of the sections A–E in the landfill 11 is based upon time of placement, it should be noted that the bottom portion of the landfill is in one set of sections, and the upper portion of the landfill containing the upper surface 19 of the landfill is in the other sections. Thus, in this example, a separation of the sections A–E based upon time of placement in the landfill also separates the upper and lower regions of the landfill so that they are part of separate sections. Accordingly, the upper sections A–C which may be more subject to weather changes are separated from the lower sections D and E which are less subject to weather variations.

After the sections A–E are selected, a plurality of samples is taken from each of the sections. The primary purpose of the sampling procedure is to obtain a representative anaerobic sample from each of the sections. The anaerobic sampling technique illustrated by way of example in FIG. 2 is preferred.

With reference to FIG. 2, a bore hole 21 is provided in the landfill 11 with the bore hole having an opening 23 at the upper surface 19 of the landfill and a rim 25 surrounding the opening at the surface 19. The bore hole 21 may be drilled by any suitable drilling apparatus 27 of conventional construction. In the embodiment illustrated, the drilling apparatus 27 includes a rotatable auger 29. A ledge 31 may be provided in the bore hole 21 below the rim 25. The ledge 31 is sufficiently wide to provide a convenient space to accommodate a workman.

In order to substantially exclude atmospheric air, a flexible sheet 33 is provided over the opening 23. The zone enclosed by the bore hole 21 and the sheet 33 constitutes an anaerobic zone 35 from which air is substantially excluded.

Although the flexible sheet 33 may take different forms, in the embodiment illustrated, it is an air impervious plastic sheet. The sheet 33 has a perimeter or periphery 37 which is held against the upper surface 19 in any suitable manner, such as by earth 39 piled on top of a peripheral region of the sheet 33. The periphery of the sheet 33 need not be sealed perfectly to the upper surface 19. Preferably, the sheet 33 is large enough so that it can extend above the surface 19 as shown in order that the workman will have sufficient head room when standing on the ledge 31.

The auger 29 is mounted on a rotatable shaft 41 which extends through a central opening 43 in the sheet 33. It is unnecessary to seal the interface between the opening 43 and the shaft 41.

Landfill gas produced by the landfill 11 migrates into the bore hole 21 and is at a pressure greater than atmospheric pressure. Consequently, the landfill gas moves upwardly in the bore hole 21 through the anaerobic zone 35 and passes out through the opening 43 and any other regions of the sheet 33 which will pass the landfill gas at the pressure differential existing between the atmosphere and the anaerobic zone. The positive pressure within the anaerobic zone 35 inflates or pushes the sheet upwardly to form a tent-like structure over the opening 23. In addition, the flow of landfill gas from the anaerobic zone 35 out through the opening 43 tends to flush or purge any air that may have existed in the anaerobic zone 35 out of this zone.

Because the gas within the anaerobic zone 35 is essentially devoid of oxygen, it is necessary to provide the workman within the anaerobic zone with his own air supply. This can be accomplished, for example, by utilizing a self-contained breathing apparatus 45 commonly known as scuba equipment. In the embodiment illustrated, the breathing apparatus 45 is placed on the upper surface 19 of the landfill 11 outside of the sheet 33, and air is supplied to the workman via a hose 47 and a face mask 49 which contains the usual mouthpiece. Although the breathing apparatus 45 could be carried on the back of the workman, his task within the anaerobic zone 35 is facilitated if the breathing apparatus 45 is left outside of the anaerobic zone as shown in FIG. 2. The face mask prevents the landfill gas from getting into the workman's eyes. Appropriate known defogging methods can be employed for the mask 49 to prevent condensation from reducing the workman's vision within the anaerobic zone 35.

The workman manually loads refuse into a sample container 51. Before this can be accomplished, it is necessary to loosen refuse from the anaerobic zone 35 within rhe bore hole 21. Although this can be accomplished in many different ways, in the embodiment illustrated, it is accomplished utilizing the auger 29 which is rotated against the area of the bore hole from which it is desired to take a sample. The auger 29 is then elevated by the drilling apparatus 27 to a location adjacent the ledge 31 where the workman can easily reach the loosened refuse. The auger 29 may loosen refuse from the very bottom of the bore hole or from a location above the bottom of the bore hole.

The workman manually loads the loosened refuse on the flights of the auger 29 into the sample container 51. This assures that the sample container 51 will be completely filled. Thereafter, the sample container is sealed so that the sample within the sample container is substantially sealed therein. The sample container is then removed from the anaerobic zone.

Although the sample container 51 can be of different constructions, in the embodiment illustrated, it includes an elongated sleeve 53 and end caps 55 and 57 with at least one of the end caps being removable. The end cap 57 has a passage 59 extending through it to the interior of the sleeve 53 and a manual valve 61 coupled to the end cap 57 in communication with the passage 59. The end cap 55 may be similarly constructed, if desired, and also be provided with a manually operable valve 60. In the embodiment illustrated, the sleeve 53 and the end caps 55 and 57 are constructed of plastic, such as PVC, and the end caps are threaded onto the sleeve 53. However, the end caps 55 and 57 could be glued to the sleeve 53, if desired. In any event, after manually loading the sample container 51 with the loosened refuse, the workman glues and/or screws the end cap 57 onto the sleeve 53, and the sample container is then removed from the anaerobic zone 35.

FIG. 4 shows an alternate sample container 51a which comprises an elongated sleeve 101 of steel or other strong material having one end closed by an end wall 103 and the other end open. The open end of the sleeve 101 has teeth 105 suitable for boring into refuse.

The open end of the sample container 51a can be closed by an end cap 107 which has a central passage 109 and a manual valve 111 coupled to the end cap in communication with the passage 109.

In use, the sample container 51 is suitably attached to the rotatable shaft 41 of the drilling apparatus 27 as by threaded fasteners 113 which extend through cooperating flanges on the shaft 41 and the closed end of the sleeve 101. The shaft 41 rotates the sample container 51a and axially advances the teeth 105 at the open end of the container into the refuse to force refuse into the sample container. Thereafter, the shaft 41 and the sample container 51a are elevated with the force of friction between the refuse and the container 51a holding the refuse within the container. The workman then screws the end cap 107 over the open lower end of the sleeve 101 within the anaerobic zone 35. Thereafter, the sample container 51a can be handled and used in the same manner as the sample container 51.

To determine the gas generation rate of the refuse within the sample container 51 in cubic feet per minute or other similar dimensions, the valve 61 can be coupled to a flow meter 63. Before beginning the test which may last for several months, the valve 61 should be opened to bleed off any previously generated landfill gas. The weight of the refuse within the sample container 51 can be determined by weighing the loaded sample container and subtracting the known weight of the unloaded sample container. Thus, the gas generation rate per pound, e.g., in cubic feet per minute per pound, of refuse can be determined.

The sample may also be used to determine the total volume of landfill gas that the sample is capable of producing. This can be accomplished, for example, by measuring the total volume of gas generated over a several-month period in the laboratory and then using available empirical data for refuse of comparable age to project the total volume of landfill gas that the sample is capable of producing. Of course, the chemical composition of the landfill gas can also be determined to ascertain among other things, the percentage of the landfill gas which is methane.

It may be desirable to subject some of the samples to certain variables to determine what effect, if any, the variables have on properties of the landfill gas, such as the rate of landfill gas generation, the total volume of landfill gas generation and/or landfill gas composition. For example, it may be desirable to add a known amount of known material to the sample. If this is to be done, a desired weight of the known material can be added to the sample container 51 through the valve 61 and the passage 59. For example, the known material may be a waste material, such as liquid cyanide compounds or chrome plating solutions or phenol-bearing wastes, which has not heretofore been deposited in the landfill 11. The weight of the known material placed into the sample container should be known. Following this, the gas generation rate, total volume of gas generated and/or the gas composition obtained from the refuse-known material sample can be determined as described above. These measured properties of the landfill gas can best be compared with the corresponding properties of the landfill gas obtained from that same sample prior to the addition of the known material. Alternatively, or in addition thereto, these measured properties can be compared with corresponding properties obtained from other samples to which the known material has not been added. Of course, various known statistical techniques can be utilized in determining the numbers of samples to be considered and the manner in which the results are processed.

The effect of temperature variations on the landfill gas from a sample can be determined by measuring the various properties of the landfill gas produced by the sample as the sample is maintained at various different temperature levels. Alternatively, different samples may be maintained at different temperatures while the properties of the landfill gas generated thereby are measured. Also, the effect of moisture flow on the landfill gas can be determined by flowing moisture through the refuse using the valves 60 and 61. Measurements made on the landfill gas generated while moisture is flowing through the sample can then be compared, for example, with similar data obtained from a sample through which moisture is not flowing. The moisture passed through the sample may be essentially water or water containing materials of known pH, buffering capacity, nutrient composition, etc.

If it is desired to ascertain the gas generation rate of the entire landfill, then at least one sample is taken from each of the sections A-E. Preferably, a multiplicity of samples is taken from each of the sections A-E at various elevations and at various horizontally spaced locations within each of the sections. The gas generation rate for each of the samples taken from the section A is then measured, and the results can be averaged or otherwise statistically processed to determine the average gas generation rate per pound of refuse within the section A. The gas generation rate per pound for the section A is then multiplied by the total number of pounds of refuse in the section A to determine the rate of gas generation for the entire section. The total weight of the section A can be approximated using various different methods. For example, the weight per unit of volume or density may first be determined by taking samples from various locations within the section. Alternatively, empirical landfill densities can be used. The volume of each section is determined by measuring the relevant dimensions of each section, and the density figure is then multiplied by the approximate volume of each section to provide the total weight of each section as of the sampling date.

An identical procedure can be followed with respect to the sections B-E. By summing the gas generation rates for each of the sections, the total gas generation rate of the entire landfill 11 can be ascertained.

Although an exemplary embodiment of the invention has been shown and described, many changes, modifications and substitutions may be made by one having ordinary skill in the art without necessarily departing from the spirit and scope of this invention.

I claim:

1. A method of obtaining a substantially anaerobic sample of refuse from a landfill comprising:
   providing a bore hole in the landfill with the bore hole having an opening at the surface of the landfill;
   substantially excluding atmospheric air from a zone which includes at least a region of the bore hole to define an essentially anaerobic zone whereby air from the atmosphere is essentially excluded from said anaerobic zone;
   loading at least some of the refuse into a sample container within the anaerobic zone to provide a sample within the sample container;

substantially sealing the sample container in the anaerobic zone so that the sample within the sample container is substantially sealed therein; and removing the sample container with the sample therein from the anaerobic zone.

2. A method as defined in claim 1 wherein said step of substantially excluding includes placing a flexible sheet over said opening of the bore hole.

3. A method as defined in claim 2 wherein the landfill produces the landfill gas under a pressure which is above atmospheric pressure, said sheet has opening means therein, and said method includes allowing the landfill gas to flow from the anaerobic zone through said opening means to the atmosphere to purge air from the anaerobic zone.

4. A method as defined in claim 1 including loosening refuse from the anaerobic zone within the bore hole and wherein said step of loading includes manually loading at least some of the loosened refuse into the sample container.

5. A method as defined in claim 4 wherein said step of loosening includes rotating an auger against some of the refuse at a first location in the bore hole and said method includes elevating at least some of the refuse loosened by said auger to a second location within the anaerobic zone utilizing said auger, and carrying out said step of manually loading adjacent said second location.

6. A method as defined in claim 1 including measuring the rate of generation of landfill gas by the sample in said sample container.

7. A method as defined in claim 1 wherein said step of loading includes providing the sample container with an open end, forcing the open end of the sample container into the refuse within the anaerobic zone to provide a sample within the sample container.

8. A method as defined in claim 7 wherein said step of loading includes rotating the sample container with the open end of the sample container being against the refuse at the bottom of the bore hole and advancing the sample container to provide the sample within the container, and said method includes elevating the open-ended sample container with the sample therein above the bottom of the bore hole.

9. A method as defined in claim 1 including contacting the sample in the sample container with a first material and thereafter measuring a property of landfill gas generated by the sample within the sample container whereby the effect of such contact with such material on said property of the landfill gas generated can be determined.

10. A method as defined in claim 1 wherein said step of substantially excluding includes placing a flexible substantially air impervious sheet over said opening of the bore hole, said bore hole having a rim at the opening of the bore hole at the surface of the landfill, the refuse in the landfill generating a landfill gas under positive pressure within the bore hole to elevate portions of said sheet above said rim, said step of loosening includes providing an auger which extends through said sheet and into the bore hole, rotating the auger against the refuse adjacent the bottom of the bore hole to loosen the refuse, and said method includes elevating at least some of the loosened refuse from adjacent the bottom of the bore hole to a location adjacent said ledge, and said step of manually loading includes manually removing at least some of the loosened refuse from the auger and manually loading such loosened refuse into the sample container.

11. A method of ascertaining the rate of land-fill gas generation by a landfill comprising:

locating a plurality of sections within the land-fill with each of the sections having a characteristic indicative of a different landfill gas generation rate;

taking at least one sample of the material of the land-fill from each of the sections substantially without introducing oxygen from the atmosphere into said samples;

allowing the samples to generate landfill gas;

measuring at least one property of the landfill gas generated from each of said samples substantially without introducing oxygen from the atmosphere into said samples; and using at least the measured property of the land-fill gas generated from said samples to make a projection concerning landfill gas generation by the landfill.

12. A method as defined in claim 11 wherein said one property is the rate of landfill gas generated from each of said samples or the total volume of gas generated by each of the samples.

13. A method as defined in claim 12 wherein the projection concerning the landfill gas generated by the landfill is the rate of landfill gas generation by the landfill or the total volume of landfill gas which can be generated by the landfill.

14. A method as defined in claim 11 wherein said one property is composition.

15. A method as defined in claim 11 including contacting one of the samples with a first material and thereafter carrying out at least a portion of said step of measuring said one property of the landfill gas generated by said one sample whereby the effect of such contact on said one property of the landfill gas generated can be determined.

16. A method as defined in claim 11 including changing the temperature of at least one of said samples to provide said one sample with a temperature of a first magnitude and thereafter carrying out at least a portion of said step of measuring said one property of the landfill gas generated by said one sample whereby the effect of said temperature change on said one property of the landfill gas generated by said one sample can be determined.

17. A method as defined in claim 11 wherein said method includes flowing moisture through said sample and carrying out at least a portion of said step of measuring said one property of the landfill gas generated by said one sample during said step of flowing whereby the effect of such moisture flow on the landfill gas generated by said one sample can be determined.

18. A method as defined in claim 11 wherein said characteristic includes time of placement of the section in the landfill.

19. A method as defined in claim 11 wherein said step of taking includes manually loading material from a first of the sections of the landfill into a sample container and substantially sealing the same container.

20. A method as defined in claim 19 wherein said step of measuring includes coupling a flow measuring device to the sealed sample container and allowing the landfill gas in the sample container to escape from the sample container through the flow meter.

21. A method as defined in claim 11 wherein said step of taking includes providing a bore hole in the land-fill with the bore hole having an opening at the surface of the landfill and with the bore hole extending into a first of said sections, substantially excluding atmospheric air from a zone which includes at least a region of the bore hole to define an essentially anaerobic zone whereby air from the atmosphere is essentially excluded from said anaerobic zone, loading some of the refuse into a sample container in the anaerobic zone, sealing the sample container in the anaerobic zone, and removing the sample container from the anaerobic zone.

* * * * *